(12) United States Patent
Kato et al.

(10) Patent No.: US 7,865,372 B2
(45) Date of Patent: Jan. 4, 2011

(54) HEALTH MANAGEMENT SYSTEM AND HEALTH MANAGEMENT METHOD

(75) Inventors: Makoto Kato, Kyoto (JP); Yuka Yamada, Nara (JP); Kiyoshi Morimoto, Hirakata (JP); Hiroshi Kutsumi, Moriguchi (JP)

(73) Assignee: Panasonic Corporation, Osaka (JP)

( * ) Notice: Subject to any disclaimer, the term of this patent is extended or adjusted under 35 U.S.C. 154(b) by 1152 days.

(21) Appl. No.: 10/491,412

(22) PCT Filed: Apr. 7, 2003

(86) PCT No.: PCT/JP03/04386

§ 371 (c)(1),
(2), (4) Date: Apr. 1, 2004

(87) PCT Pub. No.: WO03/084393

PCT Pub. Date: Oct. 16, 2003

(65) Prior Publication Data

US 2005/0010435 A1 Jan. 13, 2005

(30) Foreign Application Priority Data

Apr. 9, 2002 (JP) ............................ 2002-106173

(51) Int. Cl.
*G06Q 50/00* (2006.01)
*G06F 19/00* (2006.01)
(52) U.S. Cl. ............................................. 705/2; 705/3
(58) Field of Classification Search .................... 705/2
See application file for complete search history.

(56) References Cited

U.S. PATENT DOCUMENTS 4,718,893 A * 1/1988 Dorman et al. ............... 604/67
4,857,713 A * 8/1989 Brown ........................... 705/3
4,925,444 A * 5/1990 Orkin et al. .................. 604/80
5,279,543 A * 1/1994 Glikfeld et al. ............... 604/20
5,832,448 A * 11/1998 Brown ........................... 705/2
6,032,119 A * 2/2000 Brown et al. ................. 705/2
6,035,230 A 3/2000 Kang et al.
6,168,563 B1 1/2001 Brown
6,269,339 B1 * 7/2001 Silver ........................... 705/2

(Continued)

FOREIGN PATENT DOCUMENTS

CA 2 413 148 1/2002

(Continued)

OTHER PUBLICATIONS

Dario, Micro-systems in biomedical applications, J. Micromech. Microeng. 10 (2000)235-244.*

*Primary Examiner*—Luke Gilligan
*Assistant Examiner*—Tran Nguyen
(74) *Attorney, Agent, or Firm*—Wenderoth, Lind & Ponack, L.L.P.

(57) ABSTRACT

A health care system includes a sampling device for sampling body fluid of a test subject, an analysis device for analyzing the sampled body fluid, and a transmission device for transmitting analytical data obtained from the analysis to a diagnosis unit, where the diagnosis unit is for diagnosing a health status of the test subject from the transmitted analytical data. Moreover, the system includes a server for storing and accumulating analytical data and/or diagnostic results, and a health-care-information display device for receiving and displaying diagnostic results.

14 Claims, 7 Drawing Sheets

U.S. PATENT DOCUMENTS

| | | |
|---|---|---|
| 6,270,455 B1 | 8/2001 | Brown |
| 6,304,797 B1 | 10/2001 | Shusterman |
| 6,592,519 B1 | 7/2003 | Martinez |
| 6,669,663 B1 * | 12/2003 | Thompson .................. 604/67 |
| 6,733,446 B2 * | 5/2004 | Lebel et al. ................ 600/300 |
| 6,852,104 B2 * | 2/2005 | Blomquist ................. 604/504 |
| 7,024,369 B1 * | 4/2006 | Brown et al. ................. 705/2 |
| 2002/0029002 A1 | 3/2002 | Bardy |

FOREIGN PATENT DOCUMENTS

| | | |
|---|---|---|
| DE | 101 20 280 | 12/2001 |
| EP | 1 034 734 | 9/2000 |
| JP | 7-42999 | 2/1995 |
| JP | 2000-232963 | 8/2000 |
| JP | 2000-232964 | 8/2000 |
| JP | 2000-271097 | 10/2000 |
| JP | 2000-316820 | 11/2000 |
| JP | 2001-258868 | 9/2001 |
| JP | 2001-275996 | 10/2001 |
| WO | 98/38909 | 9/1998 |
| WO | 02/00111 | 1/2002 |
| WO | 02/25568 | 3/2002 |

* cited by examiner

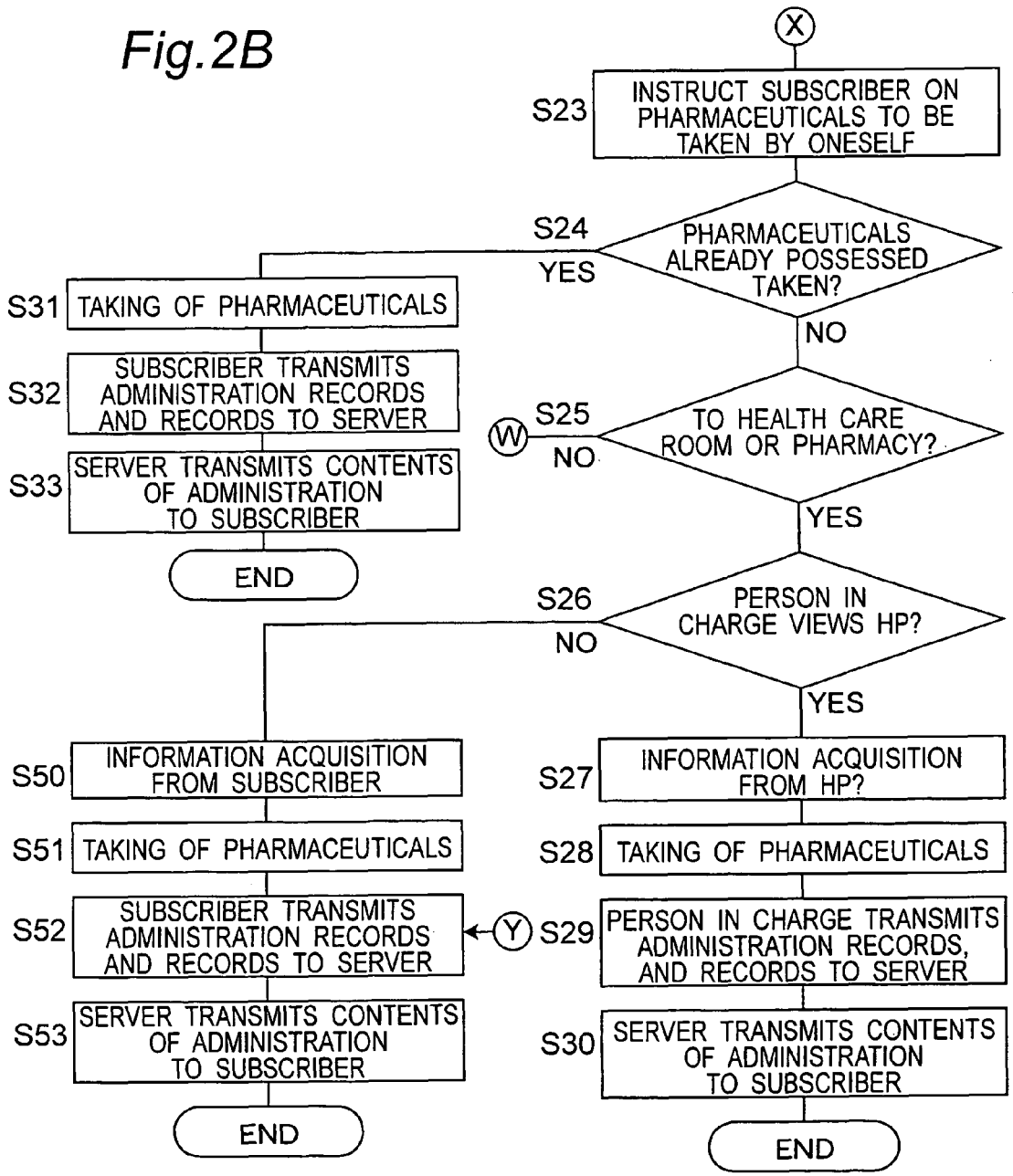

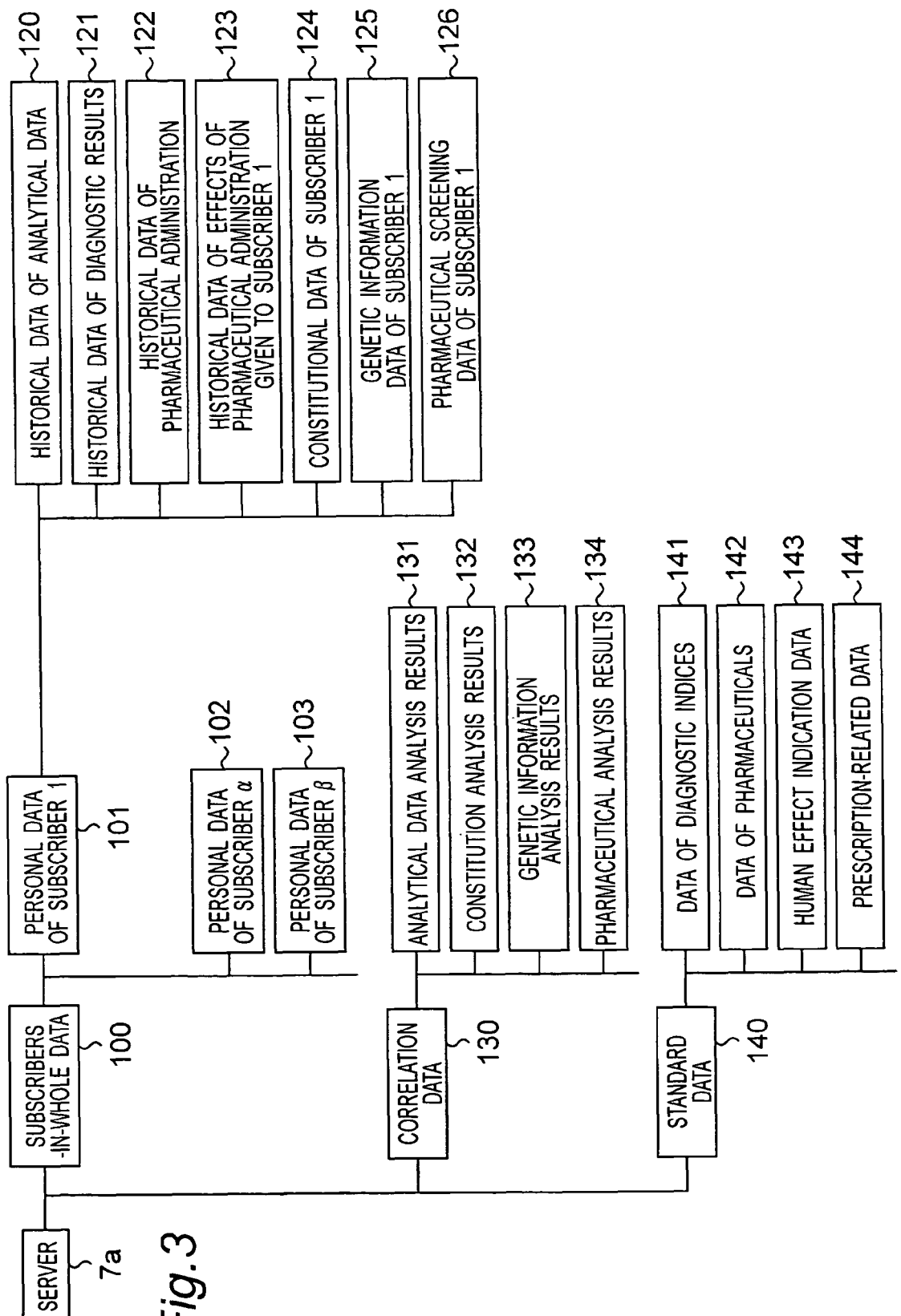

GOOD AFTERNOON. DEAR KATO
■DIAGNOSTIC RESULT:
"YOU HAVE CAUGHT A SLIGHT COLD."
■ADVICE
"TAKE VITAMIN C."
"TAKE FRUITS."
"TAKE MORE SLEEP."  END
```

GOOD MORNING.  DEAR KATO
■NOTICES
"2/4  2:40: PHARMACEUTICALS WERE
ADMINISTERED."
 【ADMINISTRATION CONTENTS】
"VITAMIN C : 100mg"
"VITAMIN E : 10mg"  END
```

GOOD MORNING. DEAR KATO
■DIAGNOSTIC RESULT:
"YOU HAVE CAUGHT A COLD"
■PRESCRIPTION
"TABLET A: TWO TABLETS AFTER
BREAKFAST"
"TABLET B: ONE AFTER BREAKFAST"
END
```

Fig.7
GOOD MORNING. DEAR KATO
■DIAGNOSTIC RESULT:
ASTHMA
■PRESCRIPTION
"THEODUR 100 mg TABLET :
FOUR TABLETS AFTER BREAKFAST"
"PREDONINE 5 mg TABLET :
TWO TABLETS AFTER BREAKFAST"
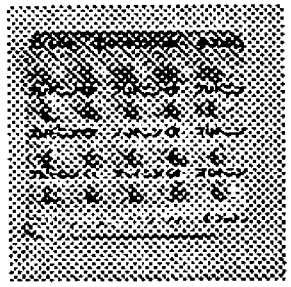

HEALTH MANAGEMENT SYSTEM AND HEALTH MANAGEMENT METHOD

BACKGROUND OF THE INVENTION

1. Field of the Invention

The present invention relates to a health care system for performing health care of test subjects.

2. Description of the Related Art

In recent years, together with the aging of the nation or with increasing prices of medical techniques, national, the national medical expenses have been increasing more and more and year by year, coming up to the issue of cracking of the health insurance society. Against such a background, it is said that there is a need for restructuring the system from the conventional medical care centered on the symptomatic treatment to another centered on preventive care. For this purpose, it is indispensable to achieve techniques for monitoring any changes in health status day by day, or to establish early diagnosis and early treatment techniques for diseases.

Also in recent years, as people have become more and more desirous of health, there have been developed body fluid tests concerned with urine, blood, and the like as a means for acquiring personal health status with accuracy. Those tests, particularly in analyses with the specimen of blood (or serum, blood plasma, etc.), make it possible to obtain a large number of bio-parameters serving as indexes of health status such as glucose concentration, lactic acid concentration, pH value, and oxygen concentration. These parameters can be known from results of blood tests at medical examinations executed by companies, schools, municipalities, or the like, or from results of blood tests at blood donation.

However, those blood tests at medical examinations or blood donations can only be known once several months or once a year or so, and thus cannot be indexes that accurately show the physical condition that changes day by day. Further, it is not practical to frequently go to medical facilities to take a blood test and get proper advice from a doctor based on acquired parameters, from a viewpoint that time and economical constraints are taken into consideration.

For these and other issues, unexamined Japanese patent publication No. 2001-258868 describes a blood analysis method and apparatus that allows a blood test to be easily carried out in the home without receiving any special training. According to this, it is taught that parameters called health markers, such as pH or oxygen concentration in blood can be monitored by daily and easily executing a blood test at home.

However, even if a person having no expertise has found the parameters, it is quite difficult for the person to connect those with a health improvement, with the result that the person would eventually ask doctors or other qualified persons for advice.

Also, unexamined Japanese patent publication No. 2001-275996 describes a health care system that the doctor transmits advice to a subject person based on biological information obtained from measurements made by the subject person at home. According to this, it becomes possible for the subject person to opportunely obtain advice useful for the person's own health care from an expert without directly visiting the medical facilities.

However, even though useful advice has been obtained, a necessity of administration of pharmaceuticals, if included in the advice, would eventually involve moving to the medical facilities or pharmacy. Thus, it can occur that the opportune advice, fortunately obtained as it has, becomes no use.

In view of the circumstances as described above, an object of the present invention is to provide a health care system and a health care method which allow a person to receive proper medical services at proper timing. More specifically, the system and method make it easily achievable for the person to maintain a good health status and prevent various diseases by receiving opportune health advice or administration of pharmaceuticals while keeping his/her own life pattern.

SUMMARY OF THE INVENTION

In order to achieve the above object, the present invention has the following constitution.

According to the present invention, there is provided a health care system comprising:

a sampling means placed within a house of a test subject person and serving for sampling body fluid of the test subject person;

an analysis means placed within the house of the test subject person and serving for analyzing the sampled body fluid;

a diagnosis means for diagnosing a health status of the test subject person from analytical data obtained by the analysis means;

a server for storing and accumulating health care information including the analytical data and/or a diagnostic result of the diagnosis performed by the diagnosis means; and a health-care-information display device which is placeable at least within the house and which serves for receiving the health care information and displaying the health care information.

Further, according to the present invention, there is provided a health care method comprising, in a state that a database is possessed in a server, the database being at least one database out of: a database of personal data which includes historical data of a test subject person such as historical data of analytical data, historical data of diagnostic results, historical data of pharmaceutical administration, and historical data of effects of pharmaceutical administration given to the test subject person, constitutional data of allergy or the like, or genetic information data, and the like of the test subject person; an integrated database which is obtained by analyzing and statistically processing the personal data of the test subject person; and a database which is of standard data such as data of diagnostic indices, data of pharmaceuticals, human effect indication data, or prescription-related data:

transmitting to a diagnosis means analytical data derived from an analysis of body fluid of the test subject person;

diagnosing a health status of the test subject person by the diagnosis means based on the analytical data and the database possessed in the server; and preparing and/or administering a pharmaceutical to the test subject person based on the diagnostic result.

According to the present invention, it becomes feasible to perform a diagnosis based on analytical data concerning the body fluid of a test subject person and perform administration and preparation of pharmaceuticals according to a result of the diagnosis, thus making it possible for the test subject person to easily fulfill health care without being burdened.

BRIEF DESCRIPTION OF DRAWINGS

These and other aspects and features of the present invention will become clear from the following description taken in conjunction with the preferred embodiments thereof with reference to the accompanying drawings, in which:

FIGS. 2A, 2B, and 2C are flowcharts of the health care system in the first embodiment of the present invention;

FIG. 3 is a data structure diagram in the first embodiment of the present invention;

FIG. 4 is a view of a disclosure-information screen in a cellular phone in the first embodiment of the present invention;

FIG. 5 is a view of a disclosure-information screen in the cellular phone in the first embodiment of the present invention;

FIG. 6 is a view of a disclosure-information screen in the cellular phone in the first embodiment of the present invention; and FIG. 7 is a view of a disclosure-information screen in a personal computer in the first embodiment of the present invention.

DETAILED DESCRIPTION OF THE INVENTION

Figure 1:
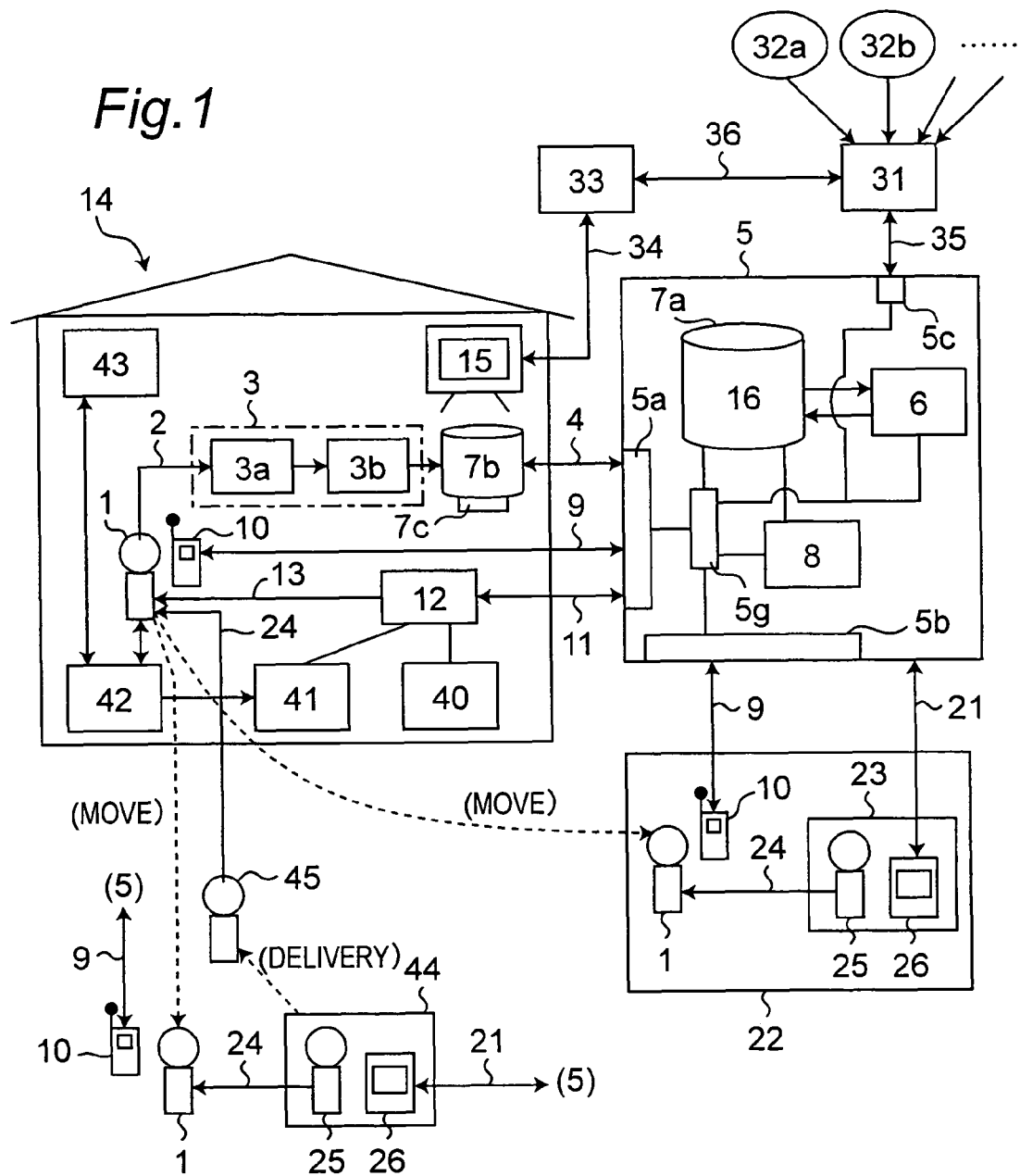
FIG. 1 is a system configuration outline view of a health care system in a first embodiment of the present invention.

Before the description of the present invention proceeds, it is to be noted that like parts are designated by like reference numerals throughout the accompanying drawings.

Hereinbelow, before embodiments of the present invention are explained in detail with reference to the accompanying drawings, various aspects of the present invention are described.

According to a first aspect of the present invention, there is provided a health care system comprising:

a sampling means placed within a house of a test subject person and serving for sampling body fluid of the test subject person;

an analysis means placed within the house of the test subject person and serving for analyzing the sampled body fluid;

a diagnosis means for diagnosing a health status of the test subject person from analytical data obtained by the analysis means;

a server for storing and accumulating health care information including the analytical data and/or a diagnostic result of the diagnosis performed by the diagnosis means; and a health-care-information display device which is placeable at least within the house and which serves for receiving the health care information and displaying the health care information.

In this case, it becomes feasible to perform the diagnosis based on the analytical data concerning the body fluid of the test subject person and perform administration and preparation of pharmaceuticals according to a result of the diagnosis, thus making it possible for the test subject person to easily fulfill health care without being burdened. For example, when the test subject person is busy, or when the distance to the medical facilities is long, the person is allowed to freely and easily fulfill the health care without being bothered to go to the medical facilities. Still, since not only diagnosis but also prescription can be provided, even those of poor medical knowledge are enabled to freely and easily fulfill the health care. Further, since the test subject person is enabled to know his/her own health status, it also becomes possible to obtain an ease of mind and moreover better the future living or reconfirm the administration of pharmaceuticals beforehand.

According to a second aspect of the present invention, there is provided the health care system as defined in the first aspect, wherein the diagnosis means and the server are placed outside the house of the test subject person; and the display device receives the diagnostic result derived from the diagnosis means placed outside the house of the test subject person and displays the diagnostic result.

According to a third aspect of the present invention, there is provided the health care system as defined in the first aspect, wherein the diagnosis means comprises an in-house diagnosis means placed within the house of the test subject person, and an out-of-house diagnosis means placed outside the house of the test subject person; and wherein the server comprises an in-house server placed within the house of the test subject person, and an out-of-house server placed outside the house of the test subject person, and in diagnosing the health status of the test subject person from the analytical data by the in-house diagnosis means, upon a decision that the analytical data have departed from a permissible range showing a state of healthiness, the in-house diagnosis means transmits the analytical data to the out-of-house diagnosis means and the out-of-house server outside the house of the test subject person, the health status of the test subject person is diagnosed from the received analytical data by means of the out-of-house diagnosis means, and after transmitting the diagnostic result made by the out-of-house diagnosis means to the display device, the diagnostic result is displayed by means of the display device.

According to a fourth aspect of the present invention, there is provided the health care system as defined in the first or second aspect, further comprising:

a pharmaceutical administration means which is placed within the house of the test subject person and which serves for preparing and/or administering a pharmaceutical to be administered to the test subject person based on the diagnostic result; and a control means which is placed within the house of the test subject person and which serves for controlling administration operation of the pharmaceutical administration means.

According to a fifth aspect of the present invention, there is provided the health care system as defined in the first or second aspect, wherein the server stores and accumulates personal data including historical data of the test subject person such as historical data of analytical data, historical data of diagnostic results, historical data of pharmaceutical administration, and historical data of effects of pharmaceutical administration given to the test subject person, constitutional data of allergy or the like, or genetic information data, and the like, and the diagnosis means performs a diagnosis based on the personal data including the historical data of the test subject person such as the historical data of analytical data, the historical data of diagnostic results, the historical data of pharmaceutical administration, and the historical data of effects of pharmaceutical administration given to the test subject person, the constitutional data of allergy or the like, or the genetic information data of the test subject person.

In this case, it becomes possible to provide the optimum diagnosis and pharmaceuticals to the test subject person.

According to a sixth aspect of the present invention, there is provided the health care system as defined in the first or second aspect, wherein the server stores and accumulates personal data including the test subject person's historical data such as historical data of analytical data, historical data of diagnostic results, historical data of pharmaceutical administration, and historical data of effects of pharmaceutical administration given to the test subject person, constitutional data of allergy or the like, or genetic information data, and the like, for making the personal data available as an integrated database that has been analyzed and statistically processed on a subscriber basis; and the diagnosis means performs a diagnosis based on the integrated database obtained by analyzing and statistically processing, on a subscriber basis, the personal data stored and accumulated in the server and including the historical data of the test subject person such as the historical data of analytical data, the historical data of diagnostic results, the historical data of pharmaceutical administration, and the historical data of effects of pharmaceutical administration given to the test subject person, the constitutional data of allergy or the like, or the genetic information data of the test subject person.

In this case, it becomes feasible to make decisions as to the health status and the tendency of disease conditions from a comprehensive viewpoint, or decisions as to the effect of cure with pharmaceuticals. Also, for newcomers of less personal data, it becomes possible to provide high-accuracy diagnosis and pharmaceuticals from comprehensive data.

According to a seventh aspect of the present invention, there is provided the health care system as defined in the first or second aspect, further comprising a disclosure means for disclosing the analytical data and/or the diagnostic result to at least any one of the test subject person, a person permitted by the test subject person, and a person permitted by a health care organization to which the test subject person belongs.

In this case, it becomes possible to protect the test subject person's privacy.

According to an eighth aspect of the present invention, there is provided the health care system as defined in the first or second aspect, wherein the analytical data and/or the diagnostic result stored and accumulated in the server are stored and accumulated in the server as the analytical and/or diagnostic result and a pharmaceutical administered to the test subject person are associated with each other.

In this case, it becomes possible to consider the relation between analytical and diagnostic results and treated pharmaceuticals, and therefore to conduct proper treatment with the test subject person.

According to a ninth aspect of the present invention, there is provided the health care system as defined in the first or second aspect, wherein the server stores and accumulates the constitutional data related to constitution of allergy or the like of the test subject person and the genetic information data of the test subject person, and wherein the diagnosis means queries the constitutional data related to the constitution of allergy or the like of the test subject person or the genetic information data of the test subject person stored and accumulated in the server to implement disclosure of advice effective for the test subject person or administration and preparation of a pharmaceutical effective for the test subject person as the diagnostic result.

In this case, it becomes possible to provide a diagnosis and pharmaceuticals suitable for the test subject person's constitution.

According to a 10th aspect of the present invention, there is provided the health care system as defined in the first or second aspect, wherein the control means controls dosing time or quantity of the pharmaceutical or type of the pharmaceutical with considerations given to a physical condition of the test subject person, pharmaceuticals that have already been administered, and pharmaceuticals that are scheduled to be administered.

In this case, it becomes possible to effectively administer proper pharmaceuticals to the test subject person to be actually administrated.

According to an 11th aspect of the present invention, there is provided the health care system as defined in the 10th aspect, further comprising a sleep-state detection means for detecting a sleep state of the test subject person, wherein after it is confirmed by the sleep-state detection means that the test subject person is in a sleep, the control means administers the pharmaceutical to the test subject person.

In this case, it becomes possible to administer pharmaceuticals to the test subject person without requiring the test subject person's attention.

According to a 12th aspect of the present invention, there is provided the health care system as defined in the fourth aspect, wherein the pharmaceutical administration means includes a pharmaceutical analysis means, and a pharmaceutical to be administered to the test subject person is analyzed by the pharmaceutical analysis means, thereby confirming that a result of the analysis agrees with the pharmaceutical described in a prescription contained in the diagnostic result.

In this case, it becomes possible to administer safer pharmaceuticals.

According to a 13th aspect of the present invention, there is provided the health care system as defined in the fourth or 12th aspect, wherein at least one of type, product name, quantity, drag price, and selling price of the pharmaceutical that has been administered to the test subject person by the pharmaceutical administration means is recorded to an area within the server where information related to the test subject person is stored and accumulated.

In this case, it becomes possible to conduct an optimum selection and pharmaceutical control for the provision of pharmaceuticals.

According to a 14th aspect of the present invention, there is provided the health care system as defined in the first or second aspect, further comprising an advertisement disclosure means for disclosing to the test subject person an advertisement of a commodity of a pharmaceutical adapted to the displayed analytical data and/or diagnostic result.

In this case, the test subject person does not need to check information on the pharmaceuticals or the like with his/her own effort, thus being allowed to easily acquire the information.

According to a 15th aspect of the present invention, there is provided the health care system as defined in the first or second aspect, wherein the diagnostic result transmitted to the test subject person is transferred to the test subject person as voice information and/or image information by an imaginary character previously set based on the test subject person's gusto.

In this case, it becomes possible to favorably and alleviatively inform the test subject person of diagnostic information, health care advice, nutritional advice, or the like. Thus, the subject person's feeling can be bettered, and actual effects of the health care system can be improved.

According to a 16th aspect of the present invention, there is provided a health care method comprising, in a state that a database is possessed in a server, the database being at least one database out of: a database of personal data which includes historical data of a test subject person such as historical data of analytical data, historical data of diagnostic results, historical data of pharmaceutical administration, and historical data of effects of pharmaceutical administration given to the test subject person, constitutional data of allergy or the like, or genetic information data, and the like of the test subject person; an integrated database which is obtained by analyzing and statistically processing the personal data of the test subject person; and a database which is of standard data such as data of diagnostic indices, data of pharmaceuticals, human effect indication data, or prescription-related data:

transmitting to a diagnosis means analytical data derived from an analysis of body fluid of the test subject person;

diagnosing a health status of the test subject person by the diagnosis means based on the analytical data and the database possessed in the server; and preparing and/or administering a pharmaceutical to the test subject person based on the diagnostic result.

In this case, the administration and preparation of pharmaceuticals according to a diagnostic result can be conducted, thus making it possible for the test subject person to easily fulfill health care without being burdened.

Now, a health care system according to a first embodiment of the present invention is explained with reference to the drawings.

It is noted that, in the first embodiment, a blood-collecting device 3a and an analysis device 3b correspond to an example of the sampling means and an example of the analysis means, respectively. Further, the Internet 4, a communication line 9, and a health care system leased line 11 correspond to examples of the first to third transmission means, respectively, and a pharmaceutical administration device 12 corresponds to an example of the pharmaceutical administration means. A personal digital assistance (PDA) including the cellular phone 10, a personal computer, and a home page (or web page on the Internet) 8 correspond to an example of the disclosure means for analytical data and/or diagnostic result (health care information) or the health care information display device. Analytical data and/or diagnostic result are an example of health care information, and the analytical data and the diagnostic result, or the analytical data, or the diagnostic result is disclosed or displayed as an example of the health care information by the disclosure means or the health care information display device.

The following description will be given on a case in which the test subject person belongs to a health care organization intended for health care or disease control over a plurality of subscribers, as an example, in the first embodiment, an enterprise's health insurance society and the health insurance society operates the health care system in detail.

In addition, needless to say, it is also preferable that the form of the health care organization that operates the health care system is a life insurance company, an enterprise conducting the business of health care, a school juridical organization, a local government, or the like without being limited only to an enterprise's health insurance society.

Also, although the description of the first embodiment will be given on an example case where the body fluid is blood, yet it is also possible that saliva, urine, lymph, or the like may be sampled and analyzed.

Figure 2A:
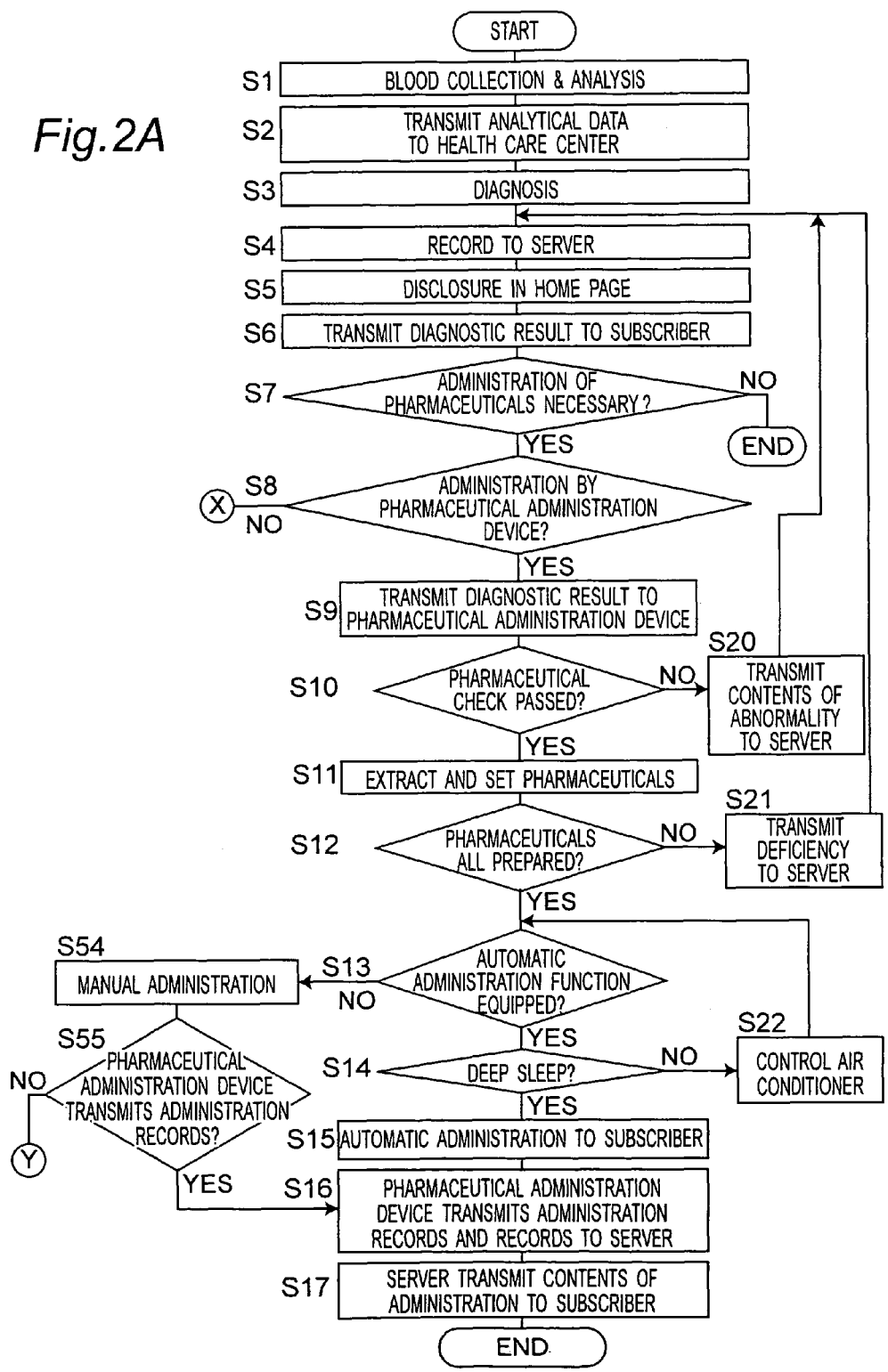
Figure 2C:
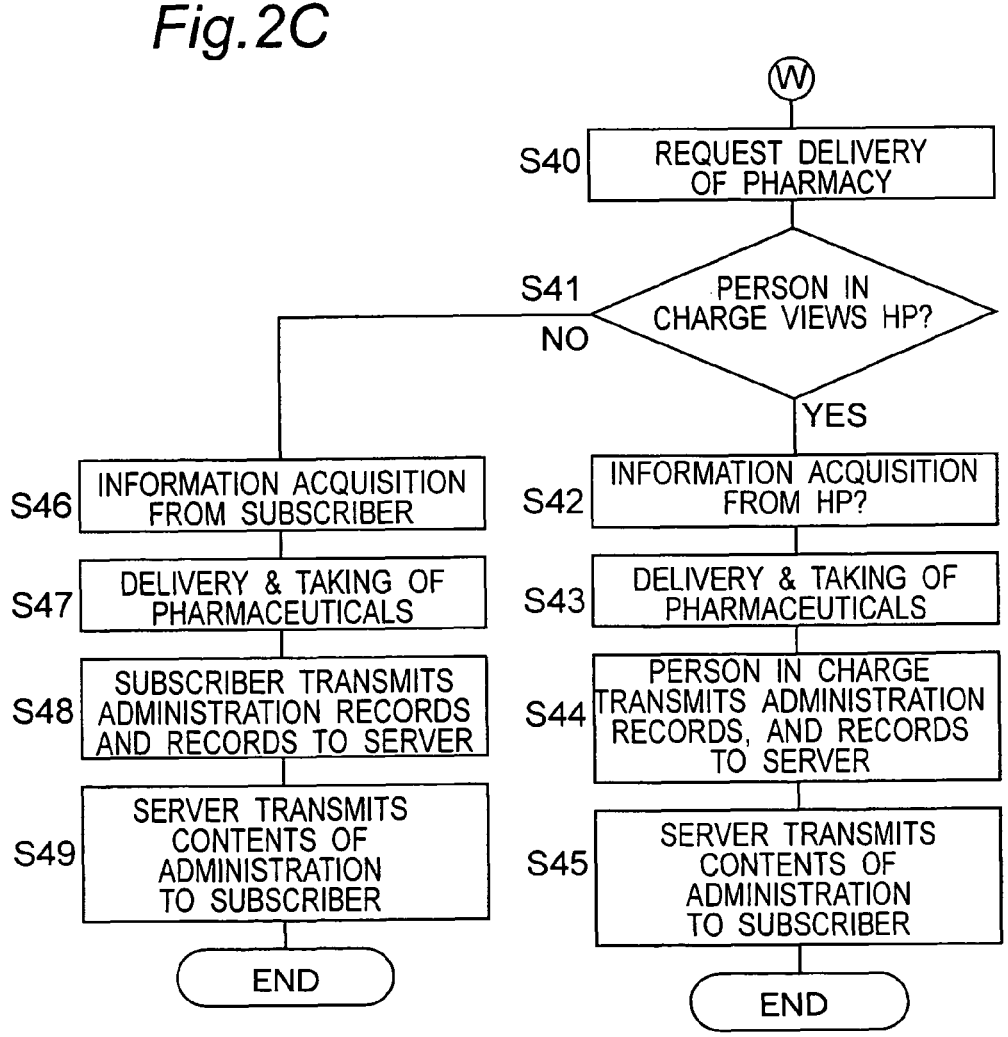

FIG. 1 shows a schematic view of system configuration of the health care system according to the first embodiment, and FIGS. 2A, 2B, and 2C show flowcharts of the health care system. A subscriber 1, who is a test subject person being a subscriber of the health insurance society, collects his/her own blood 2 at his/her own residence or home 14 by using the blood-collecting device 3a, which is an example of the sampling means, and performs a component analysis of the blood 2 by the analysis device 3b, which is an example of the analysis means (step S1 in FIGS. 2A to 2C). The blood-collecting device 3a and the analysis device 3b may be given by a blood collection-and-analysis integrated instrument 3 of the palmtop size which is generally called micro TAS (micro total analysis system), or by those intended to do the blood collection and the analysis with separate instruments, for example, to do the blood collection with an injector (a concrete example of the blood-collecting device 3a) and to do the analysis with a biochemical analyzer (a concrete example of the analysis device 3b).

Contents of the analysis differ depending on the purpose of the health care or disease control for the subscriber 1. If the principal purpose of the subscriber 1 is daily health care of the subscriber 1, then analysis items to be measured are bio-parameters serving as indices of health status such as the glucose concentration, lactic acid concentration, pH value, or oxygen concentration of the blood 2. These bio-parameters can be determined by concentration measurement by means of ISFETs (Ion-Sensitive Field Effect Transistors), absorbance measurement of a solution after chemical reaction, measurement of oxidation-reduction potential, or the like. Also, if the principal purpose is disease onset control of the subscriber 1, then microdose specimen measurement with proteome chips or antibody chips capable of analyzing proteins or antibodies that have developed within the body of the subscriber 1 is performed.

Analytical data analyzed by the analysis device 3b, after once recorded in a home server 7b installed in the subscriber's home 14, is transmitted via the Internet 4, which is an example of the first transmission means, to a transmitting/receiving section 5a of health care apparatus 5 of a health care center run by the health insurance society, and then recorded in a server 7a of the health care apparatus 5 of the health care center under the control of a control section 5g (step S2 in FIGS. 2A-2C). The control section 5g controls various operations performed by the health care apparatus 5. The transmission of analytical data to the transmitting/receiving section 5a of the health care apparatus 5 in the health care center is effected normally each time new analytical data is obtained. However, in the case where the subscriber 1 is in a good health status so that the obtained analytical data does not lead to the reception of a diagnosis, for example, in a case where it is decided from a comparison between new analytical data and the preceding-time acquired analytical data by the control means 7c of the server 7a that there are almost no changes therebetween or that there is only such a small change as to require neither pharmaceutical administration nor doctor's advice, the analytical data, without being transmitted each time, may as well be transmitted to the transmitting/receiving section 5a of the health care apparatus 5 of the health care center, for example, once a week. Consequently, in this case, there is produced a merit that the throughput of information processing by the server 7a can be reduced.

As shown in FIG. 3, in the server 7a, there has been stored and accumulated subscribers-in-whole data 100 including personal data (personal database) 101, similar personal data (personal database) 102 of another subscriber α, and similar personal data (personal database) 103 of another subscriber β, where the personal data includes past records of the subscriber 1, i.e., historical data 120 of his/her analytical data of up to the present time, data 121 of diagnostic result history (symptoms, degrees of diseases, or their degrees of progress), data 122 of pharmaceutical administration history (pharmaceuticals for treatment, dosage frequency, dosage time, dosage amount, kinds of pharmaceuticals, etc.), historical data 123 such as histories of effects (side effects or effects) of pharmaceutical administration given to the subscriber 1, constitutional data 124 of the subscriber 1 such as allergy, genetic information data 125 of the subscriber 1, pharmaceutical screening data 126, and the like. Also stored and accumulated is an integrated database or the like resulting from analyzing and statistically processing the personal data on a whole subscriber basis or on subscriber-unit bases grouped according to their ages, sexes, or districts (prefectural administrative divisions, or municipal divisions such as cities, towns, and villages, or other divisions). In this connection, the subscribers-in-whole data 100 may be given only by an integrated database without including the personal databases 101, 102, 103, . . . In this case, for example, the personal data (personal database) of the subscriber 1 is stored and accumulated in the home server 7b of the subscriber 1, the personal data (personal database) of the subscriber α is stored and accumulated in the home server 7b of the subscriber α, and the personal data (personal database) of the subscriber β is stored and accumulated in the home server 7b of the subscriber β. However, when the subscriber 1 and the subscriber α use an identical home server 7b, the personal data (personal database) of the subscriber 1 and the personal data (personal database) of the subscriber α may be stored and accumulated in the same home server 7b in a discriminable state.

Further in the server 7a, there may be contained standard data (standard database) 140 such as data 141 of diagnostic indices (symptoms, degrees of diseases, or their degrees of progress) based on general analytical data, data 142 of applied pharmaceuticals (data concerning pharmaceuticals such as pharmaceuticals for treatment, dosage frequency, dosage time, dosage amount, kinds of pharmaceuticals, etc. based on the above diagnostic indices), human effect indication data 143 of pharmaceuticals such as side effects or allergic reaction on the applied pharmaceuticals, prescription-related data 144 of pharmaceuticals such as side effects due to combinations of pharmaceuticals, and the like, in which case this standard data 140 may be used in diagnosis by the later-described diagnosis means 6. The human effect indication data 143 stored and accumulated in the database of the standard data 140 has been prepared based on precautions for use or contents of press releases published by pharmaceutical companies, and pharmaceuticals and medical devices safety information (emergency safety information, pharmaceuticals safety information, etc.) announced by the Ministry of Health, Labour and Welfare. Among others, emergency safety information announced by the Ministry of Health, Labour and Welfare is particularly important. This is information as to side effects that have been found after the sales of pharmaceuticals, and needs to be reflected on the database concurrently with the announcement.

The diagnosis means 6 automatically makes a diagnosis by a computer program based on the standard data 140 such as the personal data 101, 102, 103, . . . , the subscribers-in-whole data 100, the data 14.1 of diagnostic indices, the data 142 of applied pharmaceuticals, the human effect indication data 143, and the prescription-related data 144 of pharmaceuticals (step S3 of FIGS. 2A-2C).

The diagnosis means 6, which performs diagnosis operations under the control of the control section 5g, for example, analyzes symptoms or the like by analytical data transmitted from the home server 7b of the test subject person to the transmitting/receiving section 5a of the health care apparatus 5 of the health care center, and by the data 141 of diagnostic indices, thereby determining pharmaceuticals or the like applied according to the data 142 of pharmaceuticals. In this process, the diagnosis means 6 takes into consideration further considerations so that the pharmaceuticals applied based on the human effect indication data 143 or the prescription-related data 144 are more suited to the test subject person.

The above diagnosis has been made based on the analytical data and the standard data 140. Otherwise, the diagnosis may also be made based on personal data, for example, it is also possible to consider comprehensive decisions as to the person's symptoms (decisions as to whether the symptoms or the health status has undergone successful transitions from the past, or has not been improved, or other decisions, or a decision as to new symptoms) based on the history of analytical data of the person and the history of diagnostic results, or an optimum selection of pharmaceuticals for the relevant person based on the human effect indication data 143, or combinations of pharmaceuticals that involve less side effects or less pharmaceutical dosage amount and pharmaceutical dosage frequency based on the prescription-related data 144.

The reasons of considering not only the historical data 120 of analytical data and the data 121 of diagnostic-result history but also various types of other information in making the diagnosis are described below. Among pharmaceuticals, there are some types of ones that will produce very useful effects for some persons, but that will give unnecessary effects for others. Side effects are typical examples thereof, and there are some cases where the pharmaceuticals have larger effects in side effects than in pharmaceutical effects. Factors related to side effects can be exemplified by interactions with currently administered other pharmaceuticals or the person's constitution. In view of these points, a diagnosis including the prescription of pharmaceuticals is conducted after fully checking interactions of pharmaceuticals scheduled to be administered with other pharmaceuticals administered in the past or other pharmaceuticals being currently administered, reactions of previous administration of the same pharmaceuticals, known influences given by the pharmaceuticals to such constitutions as allergy, genetic affinities with pharmaceuticals that differ among individuals, or the like. For example, terfenadine, which is one kind of antihistamine, is known as a medicine for allergic rhinitis and urticaria or a medicine that suppresses attacks of bronchial asthma, and it is assumed that sufficient precautions are needed for its prescription and dosage of terfenadine. In the relation of terfenadine with constitution, terfenadine is designated as a contraindication to those having liver function disorder, those having cardiac failure, cardiac infarction, and bradycardia, and the like. Also, in relations of terfenadine with other pharmaceuticals, its use with itraconazole, miconazole, or like other pharmaceuticals is designated as a contraindication because of a possibility that side effects of the cardiovascular system such as ventricles arrhythmia may appear. Further, also in the relation between terfenadine and foods, there have been clinical test results that its simultaneous administration together with grapefruit juice caused the recognition of changes in conditions, although it could not be said to be a side effect symptom. In addition, as Troglitazone (trade name: NOSCAL), which is an antidiabetic drug, has side effects that could cause a serious hepatopathy and was stopped from sale in 2000, its side effects were found to be due to a factor of defects of specific genes. In order to avoid these and other adverse effects, preferably, the human effect indication data 143 showing possible side effects or allergic reaction or the like and the prescription-related data 144 showing side effects due to combinations of pharmaceuticals are preparatorily built up into a database as the standard data 140 with respect to all of pharmaceuticals that this system can prescribe for subscribers, the individual person-basis constitutional data 124, the genetic information data 125, the historical data 122 of pharmaceutical administration, the historical data 123 of effects of pharmaceutical administration given to the subscriber 1, and the like are preparatorily built up into a database as personal data 101, 102, 103, . . . , and pharmaceuticals that could cause adverse effects on the relevant subscriber due to their administration are built up into a database as pharmaceutical screening data 126 by checking personal data for standard data from subscriber to subscriber. Once the pharmaceutical screening data 126 has been prepared, it is no longer necessary to query the standard database and the personal database at each time of prescription, hence quite high efficiency.

In this connection, the analytical data are preferably recorded in association with pharmaceuticals that were administered to the subscriber 1. Since effects of the pharmaceutical administration have been reflected on the analytical data, recording and accumulating the kinds of administered pharmaceuticals and their effects with respect to the subscriber 1 in correlations therebetween means screening effective pharmaceuticals and less effective pharmaceuticals for the subscriber 1, so that the more the data are accumulated, the more the administration of pharmaceuticals can be effective.

Also, as shown in FIG. 3, data showing correlations among constitution, administered pharmaceuticals, analytical data, and the like, such as data 131 of analytical-data analysis results, data 132 of constitution analysis results, data 133 of genetic-information analysis results, and data 134 of administered-pharmaceuticals analysis results are preparatorily stored in the server 7a from the accumulated data of all the subscribers so as to be built up into a database as correlation data 130. Then, by performing further analyses and examinations based on this database, it becomes possible to fulfill effective pharmaceutical administration even for those subscribers who have just joined the system and whose own personal data have been less accumulated.

For example, by referring to data of a subscriber (subject person) whose constitution is similar to a first-time subscriber and whose data have already been accumulated, it becomes possible to fulfill more proper diagnosis and the provision of pharmaceuticals even for the first-time subscriber by using the referenced subject person's analytical data, data 121 of diagnostic result history, historical data 122 of pharmaceutical administration, and the like. Given pharmaceuticals X and Y for one disease case A, in order to make it known beforehand which of them is more effective and safer to administer, the correlation database of the correlation data 130 is preferably used. Within the correlation database are accumulated analytical data of all the subscribers in various cases, as the data 131 of analytical-data analysis results including, for example, "analytical data results in a case where the case A appeared to a person of constitution B and where the pharmaceutical X was administered," and "analytical data results in a case where the case A appeared to a person of constitution B and where the pharmaceutical Y was administered," and "analytical data results in a case where the case A appeared to a person of constitution C and where the pharmaceutical X was administered," and the like. The diagnosis means 6 can offer optimum prescriptions based on considerations of the subscriber 1's intent (cost, dosage amount, or dosage timing etc.) in addition to the data 131 of analytical-data analysis results.

It is also useful to exploit this correlation database for research and development of new pharmaceuticals.

For example, by analyzing and examining in detail the correlation database formed from correlations among the constitution-analysis result data 132, the administered-pharmaceuticals analysis result data 134, the analytical-data analysis result data 131, and the like, from the accumulated data of all the subscribers, it becomes implementable to take into account the effects of pharmaceuticals administered to a symptom of a one-type-of-constitution person to develop pharmaceuticals suited to the person's constitution.

It becomes also implementable to grasp an issue of unimproved symptom or constitution based on the correlation database to thereby progress research and development specialized to the issue.

Thus, by using the correlation database, it also becomes possible to progress the development of pharmaceuticals in line with the actual circumstances and to reduce periodical and economic losses for development of pharmaceuticals that involve trial and error.

By further referring to the personal data in addition to the correlation database, it also becomes possible to progress the development of pharmaceuticals suited to the person.

It is noted here that although the diagnosis means 6 performs the processing by reading various types of data such as analytical data from the server 7a in the above case, it is also possible that various types of data are not stored in the server 7a, but the diagnosis means 6 itself may contain those data individually.

Further, the diagnosis means 6 may also be one without problem in which, under the control of a control section 4g, information as to a diagnosis performed by the diagnosis means 6 based on the records stored and accumulated in the server 7a is transmitted from the transmitting/receiving section 5a of the health care apparatus 5 of the health care center to personal computers or personal digital assistants (PDAs) of qualified persons such as doctors, pharmacists, and dietitians, asking qualified persons for a decision as to the properness of the diagnostic information, and in which decision results are received by the transmitting/receiving section 5a of the health care apparatus 5 of the health care center, and then the diagnostic information is corrected to a more proper diagnosis by the diagnosis means 6, thus a diagnosis being formed.

The diagnostic results are recorded to the server 7a, like the analytical data, as the historical data 121 of diagnostic results (step S4 in FIGS. 2A to 2C). The diagnostic results are preferably recorded as the historical data 121 of diagnostic results in association with the pharmaceuticals administered to the subscriber 1, also like the analytical data. The historical data 120 of analytical data, the historical data 121 of diagnostic results, and the historical data 122 of administered pharmaceuticals are also preferably recorded in association. Although a prescription of pharmaceuticals is included in the diagnostic results, combinations of pharmaceutical kinds recently administered and pharmaceuticals to be administered this time can include such pharmaceuticals as could cause new side effects and that are not present in the database. In order to avoid such administration, it is desirable that pharmaceuticals administered to the subscriber 1 and diagnostic results are recorded in association with each other.

Also, analytical-data and diagnostic-result records of the subscriber 1 are disclosed in a home page (or a web page on the Internet) 8 of the health care center, which is an example of the disclosure means that can be controlled by the health care apparatus 5 of the health care center (step S5 in FIGS. 2A to 2C). Those who can access the home page are persons who have been subjected to the checking of ID number, password, or personal authentication or the like and who have passed this, that is, permitted ones among the subscribers 1 and persons of health insurance societies to which the health care apparatus 5 of the health care center for primarily performing the diagnosis of test subject persons as well as the test subject persons of subscribership belong. It is noted that the disclosure means, not limited to the home page (or web page on the Internet) 8, may well be a system, as an example, in which when an access applicant has posed a request for information disclosure to the health care center, the transmitting/receiving section 5a of the health care apparatus 5 of the health care center transmits a reply to the access applicant as encrypted data.

The diagnostic results formed by the diagnosis means 6 are transmitted by the transmitting/receiving section 5a of the health care apparatus 5 of the health care center under the control of the control section 5g from the server 7a via a communication line 9, which is an example of the second transmission means and which is provided for personal digital assistants (PDAs) including cellular phones and the like, to the cellular phone 10, which is an information terminal device such as a personal digital assistant (PDA) owned by the subscriber 1 and which is an example of the disclosure means or health-care-information display device (step S6 in FIGS. 2A - 2C). In the first embodiment, the following description is given by using the cellular phone 10 as an example of the disclosure means or health-care-information display device which can be placed at least within the residence and which serves for receiving the health care information and displaying the health care information.

In this way, the subscriber 1 is allowed to know his/her own diagnostic results. FIG. 4 shows an example of disclosure information to be disclosed on the screen of the cellular phone 10. In FIG. 4, "You have caught a slight cold" is displayed as a diagnostic result. Further, "Take vitamin C", "Take fruits", and "Take more sleep" are displayed as advice in addition to the diagnostic result. The advice in addition to the diagnostic result includes such pieces of advice as health care advice, nutritional advice, mental hygiene-related advice, or others useful for the subscribers' health care. With reference to these, the subscriber 1 is enabled to fulfill daily health care by reflecting these pieces of advice on his/her meals, exercise, sleeping, or other actions. In the case shown in FIG. 4, a prescription of pharmaceuticals given to the subscriber 1 is not included in the diagnostic result, and no more than advice is given. In such a case, the operations of this health care system come to an end at this point (step S7 in FIGS. 2A-2C).

Next described is a case where a prescription of pharmaceuticals given to the subscriber 1 is included in the diagnostic result. The diagnostic result is transmitted from the transmitting/receiving section 5a of the health care apparatus 5 of the health care center via a health-care-system exclusive line 11, which is an example of the third transmission means, to the pharmaceutical administration device 12 that prepares pharmaceuticals to be administered to the subscriber 1 (steps S6-S9 in FIGS. 2A-2C). A prescription for pharmaceuticals (data on administered pharmaceuticals) is included in the diagnostic result, and the pharmaceutical administration device 12 extracts and set pharmaceuticals 13 that should be administered to the subscriber 1 from within an unshown pharmaceutical stock according to this prescription (step S11 in FIGS. 2A-2C). Referring to a concentrate example, when the prescription describes "Administration: liquid drug A, 0.1 g", the pharmaceutical administration device 12 sets a portion of 0.1 g from the liquid drug A in the pharmaceutical stock to a syringe. Then, the pharmaceuticals 13 set in the pharmaceutical administration device 12 are administered to the subscriber 1 (step S15 in FIGS. 2A-2C).

In this case, it is much preferable that the pharmaceutical administration device 12 includes the pharmaceutical analysis means 40 (step S10 in FIGS. 2A-2C). It can potentially occur with high possibility that another liquid drug B may be erroneously disposed at a place where the liquid drug A should be disposed. In such a case, in order to avoid any misadministration in advance, the pharmaceutical analysis means 40 analyzes the pharmaceuticals before setting the pharmaceuticals to the syringe, checking to confirm whether actual kinds of pharmaceutical are in correspondence to the kinds of pharmaceuticals described in the prescription (step S10 in FIGS. 2A-2C). As a result of the confirmation, if the pharmaceutical that should be a liquid drug A is not a liquid drug A, the pharmaceutical administration device 12 immediately stops the operation of administration to the subscriber 1, transmitting occurrence of an abnormality to the transmitting/receiving section 5a of the health care apparatus 5 of the health care center (steps S10, S20 in FIGS. 2A-2C), where contents thereof are stored and recorded to the server 7a under the control of the control section 5g (step S4 in FIGS. 2A-2C). Also, the health care apparatus 5 of the health care center, under the control of the control section 5g, contacts the cellular phone 10 of the subscriber 1, giving instructions for correction of the mis-disposition and administration of the liquid drug A in another way. Further, as a result of the confirmation, if the pharmaceutical that should be a liquid drug A is a liquid drug A, the pharmaceutical is extracted and set (step S11 in FIGS. 2A-2C).

Preferably, the pharmaceutical analysis means 40 is implemented by a micro TAS (Micro Total Analysis System) The micro TAS capable of analysis with infinitesimal amounts of samples is much preferred from the viewpoint of eliminating waste of the pharmaceuticals 13. As shown above, confirming the pharmaceuticals 13 to be administered makes it possible to ensure the subscribers' safety and to provide an ease of mind as well.

These sequential operations of the pharmaceutical administration device 12 are carried out under the control of the control means 41, more specifically, under the control of the control means 41 that has received a control signal from the control section 5g driven and controlled by a control program 16 present in the server 7a of the health care apparatus 5 of the health care center. The control program 16 is a computer program, which controls the pharmaceutical administration device 12 from the transmitting/receiving section 5a of the health care apparatus 5 of the health care center via the health-care-system exclusive line 11.

It is noted that the control program 16 may be provided in an arithmetic unit built in the pharmaceutical administration device 12, may control the pharmaceutical administration device 12, and may be provided in-the home server 7b.

In this case, in detail, the configuration may be as follows. For example, the diagnosis means 12, 6 for diagnosing the health status of the subscriber 1 from analytical data are implemented by a pharmaceutical administration device 12 which functions as the in-house analysis means disposed within the subscriber 1's home 14, and the diagnosis means 6 which functions as the out-of-house diagnosis means disposed outside the subscriber 1's home 14. Also, the servers 7b, 7a are implemented by an in-house server 7b disposed within the subscriber 1's home 14, and an out-of-house server 7a disposed outside the subscriber 1's home 14. Further, in a case where a diagnosis of the subscriber 1's health status is performed from the analytical data by the pharmaceutical administration device 12, which is the in-house diagnosis means, and where it has been decided that the analytical data has departed from a permissible range showing a state of healthiness, the analytical data are transmitted to the diagnosis means 6, which is the out-of-house diagnosis means outside the subscriber 1's home 14, and the out-of-house server 7b. In another case where a diagnosis of the subscriber 1's health status is performed from the analytical data by the pharmaceutical administration device 12, which is the in-house diagnosis means, and where it has been decided that the analytical data fall within the permissible range showing a state of healthiness, the analytical data are not transmitted, while the state of healthiness is displayed by the cellular phone 10, which is an example of the display device. From the received analytical data, the subscriber 1's health status is diagnosed by the diagnosis means 6, which is the out-of-house diagnosis means, and the diagnostic result by the diagnosis means 6, which is the out-of-house diagnosis means, is transmitted to the cellular phone 10 so that the diagnostic result is displayed thereon.

The control program 16 (or control section 5g) is capable of producing additional large effects by controlling the time of administration to the subscriber 1. For example, it becomes possible to administer a plurality of kinds of pharmaceuticals which, if administered simultaneously, could potentially cause side effects, to the subscriber 1 with a time lag. Thus, by the control program 16 (or control section 5g), it becomes possible to perform the administration to the subscriber 1 by taking into consideration pharmaceuticals that have already been administered or pharmaceuticals that are to be administered.

Further, during the control by the control program 16 (or control section 5g), it is also possible to perform the control of dosage time or amount or types of pharmaceuticals to be administered, as well as the operations, by grasping the physical condition of the subscriber 1 from the subscriber 1's perspiration, brain-wave data, and analytical data.

Furthermore, in terms of the control of dosage time, it is desirable that the administration of the pharmaceuticals 13 to the subscriber 1 be performed automatically while the subscriber 1 is sleeping (steps S13, S14 in FIGS. 2A-2C). As to the reason of this, taking pharmaceuticals day by day is generally quite cumbersome and, in particular, it is troublesome for those who are free from any particular abnormalities in physical condition to take pharmaceuticals only for health maintenance. Also, one is in a rest state while sleeping, and so the pharmaceuticals 13 can be administered without a fear for abrupt exercises.

As the method of fulfilling automatic administration during the subscriber 1's sleep, whereas a method of preparatorily setting a drip before bedtime is available, a needleless pressure syringe ShimaJET made by Shimadzu Corporation is preferable as an instrument for preferably implementing the pharmaceutical administration device 12 that enables the automatic administration. This product is characterized by the absence of an injection needle and, instead, so constructed as to inject that a pharmaceutical is directly subcutaneously jetted instantaneously by high pressure through a small hole of a nozzle tip end. The elimination of the injection needle allows the user to enjoy such merits as a relief from pain and strain at a needle puncture, a decrease of accidents such as fracture of the injection needle, and a reduction of pharmaceutical administration time. With this 'ShimaJET', for example, if the pharmaceuticals 13 are administered from the sole of the foot of the subscriber 1, then the pharmaceuticals 13 can be administered without giving any pain to the subscriber 1 even during a sleep (step S13 in FIGS. 2A-2C).

In the case where the automatic administration function is not provided, the subscriber 1 takes the pharmaceuticals 13, for example, by manually driving the pharmaceutical administration device 12 (step S54 in FIGS. 2A-2C). In this case also, if the pharmaceutical administration device 12 transmits administration records to the transmitting/receiving section 5a of the health care apparatus 5 of the health care center, administration records are automatically transmitted by the pharmaceutical administration device 12 (steps S55, S16 in FIGS. 2A-2C)

In this connection, it is much preferable to provide a sleep-state measuring device 42 for detecting that the subscriber 1 is in a sleep state. When the administration device applies an operation to such a subscriber as described above, it has to be avoided that the subscriber 1 suddenly moves during the administration of the pharmaceuticals 13, and the administration is desirably conducted in the subscriber 1's so-called deep sleep state. For this purpose, it is also possible, for example, to monitor the subscriber 1's motions by a video camera and administer the pharmaceuticals 13 at a timing captured around a motion stop. Further, it is also preferable to check the correlations among the subscriber 1's perspiration, brain-wave data, bedtime, time elapsed from the start of sleep, body temperature, and the like, and analyze the timing at which the subscriber 1 is in a deep sleep. Moreover, it is preferable as well to control ambient environments such as room temperature while monitoring the body temperature of the subscriber 1 by a thermograph so as to facilitate the preparation of an environment for the subscriber 1's deep sleep.

FIG. 1 shows a case in which the sleep-state measuring device 42 controls an air conditioner 43 (steps S14, S22 in FIGS. 2A-2C). When the sleep-state measuring device 42 has decided that the subscriber 1 is not in a deep sleep state, then the sleep-state measuring device 42 controls the air conditioner 43 to facilitate the preparation of an environment for the subscriber 1's deep sleep. The sleep-state measuring device 42 normally monitors the sleep state of the subscriber 1 and, when having decided that the subscriber 1 has fallen into a deep sleep, actuates the pharmaceutical administration device 12 to execute the pharmaceutical administration to the subscriber 1.

As to a concrete example of measurement and control of sleep state, according to a technique disclosed in unexamined Japanese patent publication No. 07-42999, it is implementable to measure sleep statuses including the subscriber having fallen into a sleep, his/her falling into a deep sleep, the sleep being a REM sleep, and the like by measuring the deep body temperature at a forehead portion of the subscriber 1. Moreover, whereas it has been proved that one is in a deepest sleep at a deep body temperature of 35° C. of the forehead portion, there has also been disclosed a technique that the sleep state of the subscriber 1 is controlled by performing such air-conditioning control as decreasing the room temperature by one degree in response to a 0.5° C. increase of the deep body temperature of the forehead portion from that of 35° C.

The control means 41 is associated with the sleep-state measuring device 42, and the pharmaceutical administration device 12 is controlled by the control means 41 based on results measured by the sleep-state measuring device 42.

In the case where the automatic administration function is provided (step S13 in FIGS. 2A-2C), the pharmaceutical administration device 12, after performing the automatic pharmaceutical administration to the subscriber 1 (step S15 in FIGS. 2A-2C), transmits administration records, i.e. information as to the fact of the administration's having been done and the types, product names, quantities, drug prices, and the like of the pharmaceuticals 13, to the transmitting/receiving section 5a of the health care apparatus 5 of the health care center via the health-care-system exclusive line 11, and the administration records are recorded to the server 7a (step S16 in FIGS. 2A-2C). Further, similar record contents may be recorded to the home server 7b. For verification of the subscriber 1, the record contents are transmitted from the transmitting/receiving section 5a of the health care apparatus 5 of the health care center to the cellular phone 10 (step S17 in FIGS. 2A-2C). FIG. 5 shows an example of a disclosure-information screen to be displayed on the screen of the cellular phone 10. In FIG. 5, "2/42:40: Pharmaceuticals were administered" is displayed. Also, as the contents of administration, "Vitamin C: 100 mg" and "Vitamin E: 10 mg" are displayed. Like this, the disclosure information includes administration time, drug name, quantity, and the like.

Thus, the control means 41 that controls administration operations by the pharmaceutical administration device 12 (an example of the pharmaceutical administration means) evaluates the association between a diagnostic result and the pharmaceuticals 13, and performs a decision process as to the presence or absence of an administration operation, a reconfirmation process for the diagnosis means 6, or a report to the test subject person. For example, an analysis is performed on the actual pharmaceuticals 13 by the pharmaceutical analysis means 40 as described above, or a decision is made as to a mere data-basis consistency between the diagnostic result data and the pharmaceutical 13 data, where if it is decided that there is an error between the diagnostic result and the pharmaceuticals 13 or that there is an error in dosage amount, a confirmation is made beforehand so as to further assure the safety of the subject person to which the pharmaceuticals 13 are administered. Also, urging the subject person to make reports makes it possible to provide an awaking to health care as well as an ease of mind to the subject person.

Further, the physical-condition detection means for detecting health status and biorhythm of the test subject person, or a timer, is further provided, and the pharmaceuticals 13 are administered in consideration of the physical condition of the test subject person or the dosage time of the pharmaceuticals 13. As a result of this, it becomes possible to administer the pharmaceuticals 13 by taking into consideration the subject person's feeling, the dosage timing of the pharmaceuticals 13 (between meals, after meals, etc.).

Also, although the selection of the pharmaceuticals 13 is done on the server 7a side in the first embodiment, it is also possible that the control means 41 itself is provided with data concerning the constitution such as allergy of the test subject person and/or data of the pharmaceuticals 13 that are currently administered, where pharmaceuticals 13 to be administered are selected based on the data concerning the constitution and the data concerning the pharmaceuticals 13. As a result of this, also in actual administration, it becomes possible to fulfill administration of pharmaceuticals 13 that match the constitution of the subject person or that cause less side effects with the currently administered pharmaceuticals 13.

Further, in the case where the pharmaceutical administration device 12 has no automatic administration function or where the extracted pharmaceutical 13 is such a type of pharmaceutical that cannot be automatically administered such as internal medicines, the subscriber 1 himself/herself takes the pharmaceutical by using the pharmaceutical administration device 12 (steps S13, S54 in FIGS. 2A-2C). The pharmaceutical administration device 12 in this case may offer the pharmaceuticals 13 in a pharmaceutical stock such as a medicine box that is used by the subscriber for administration. The administration records may be transmitted by the pharmaceutical administration device 12 from the transmitting/receiving section 5a of the health care apparatus 5 of the health care center via the health-care-system exclusive line 11 (steps S55, S16 in FIGS. 2A-2C) or may be done by the subscriber 1 via a cellular phone line 9 (step S52 in FIGS. 2A-2C). In either case, administration records transmitted to the transmitting/receiving section 5a of the health care apparatus 5 of the health care center are recorded to the server 7a, and the record contents are transmitted from the transmitting/receiving section 5a of the health care apparatus 5 of the health care center to the cellular phone 10 of the subscriber 1, for confirmation's sake (steps S17, S53 in FIGS. 2A-2C). In the case where all of the pharmaceuticals that should be administered to the subscriber 1 have been administered thereto over the above operations, the operations of this health care system come to an end.

Further, a case where the pharmaceutical administration device 12 is not present in the home 14 of the subscriber 1 is explained. In this case, the subscriber 1 takes the pharmaceuticals 13 by himself/herself according to the prescription shown in the diagnostic result transmitted from the transmitting/receiving section 5a of the health care apparatus 5 of the health care center to the cellular phone 10 (steps S8, S23 in FIGS. 2A-2C). FIG. 6 shows an example of disclosure information to be disclosed on the screen of the cellular phone 10. In FIG. 6, "You have caught a cold" is displayed as a diagnostic result. Further, in the prescription in addition to the diagnostic result, "Tablet A: Two tablets after breakfast" and "Tablet B: One tablet after breakfast" are displayed. In the case where the subscriber 1 has already possessed the pharmaceuticals 13 disclosed here, the subscriber 1 takes the pharmaceuticals 13 according to the prescription (steps S24, S31 in FIGS. 2A-2C). Then, the subscriber 1 transmits administration records via the cellular phone line 9 to the transmitting/receiving section 5a of the health care apparatus 5 of the health care center (step S32 in FIGS. 2A-2C). The transmitted administration records are recorded to the server 7a, and the record contents are transmitted from the transmitting/receiving section 5a of the health care apparatus 5 of the health care center to the cellular phone 10 of the subscriber 1, for confirmation's sake (step S33 in FIGS. 2A-2C).

In the case where all of the pharmaceuticals 13 that should be administered to the subscriber 1 have been administered thereto over the above operations, the operations of this health care system come to an end.

It is noted that the diagnostic result including the prescription transmitted to the subscriber 1, other than the display on the cellular phone 10, may also be provided in such a way that the subscriber 1 accesses the home page 8 (step S5 in FIGS. 2A-2C), or that the health care apparatus 5 of the health care center transmits the diagnostic result as an e-mail to the subscriber 1 so as to allow the subscriber 1 to view this. In the case where a home page or an e-mail is utilized, a personal computer is used and therefore information more specific than the cellular phone 10 can be viewed. For example, as shown in FIG. 7, inserting package photographs of pharmaceuticals to be administered can make the likelihood of misuse lower than when only text information is transmitted. In FIG. 7, "Asthma" is displayed as a diagnostic result. Also, in the prescription in addition to the diagnostic result, "Theodur 100 mg tablet: Four tablets after breakfast" and "Predonine 5 mg tablet: Two tablets after breakfast" are displayed, while photographs of the individual tablets are also displayed.

Next, a case where the pharmaceutical 13 which should be administered to the subscriber 1 is not present (steps S24, S25 in FIGS. 2A - 2C), or is in short supply (steps S12, S21 in FIGS. 2A - 2C), in the pharmaceutical stock is explained. The pharmaceutical administration device 12 transmits information including the types, product names, quantities, drug prices, and the like of the pharmaceuticals 13, which should be administered but could not be done to the subscriber 1, to the transmitting/receiving section 5a of the health care apparatus 5 of the health care center via the health-care-system exclusive line 11, and records the information to the server 7a (steps S21, S4 in FIGS. 2A - 2C). Then, the information as to the pharmaceuticals 13 that were not administered is transmitted to the subscriber 1 from the transmitting/receiving section 5a of the health care apparatus 5 of the health care center via the cellular phone line 9, and the subscriber 1 administers the pharmaceuticals 13 by himself/herself in some other way (steps S4 to S8, S23, S24, S31, S25 in FIGS. 2A - 2C).

In most cases, the subscriber 1 goes out from his/her home 14 and goes to company or school day by day. Hereinbelow, a description is given on a case where the subscriber 1 works at a company 22. The subscriber 1 visits a health care room 23, which is provided in the company 22 or which is a section tied up with the company 22 and takes charge of health care for employees of the company 22 (step S25 in FIGS. 2A-2C). A person 25 in charge of the health care room 23 distributes pharmaceuticals 24 to the subscriber 1. The distributed pharmaceuticals 24 may be based on information which has been acquired by the person 25 accessing the home page 8 with a permission obtained from any one of the subscriber 1, the health care apparatus 5 of the health care center, and the health insurance society via the Internet 21, which is an example of the fourth transmission means, and a transmitting/receiving section 5b of the health care apparatus 5 of the health care center by using a personal computer 26 (steps S26, S27 in FIGS. 2A-2C), or may be based on information transmitted from the transmitting/receiving section 5b of the health care apparatus 5 of the health care center to the cellular phone 10 of the subscriber 1 (step S50 in FIGS. 2A-2C).

Upon completion of the distribution and administration of the pharmaceuticals 24 to the subscriber 1 (steps S28, S51 in FIGS. 2A-2C), administration records including the types, product names, quantities, drug prices, selling prices, and the like of the pharmaceuticals 24 are transmitted to the transmitting/receiving section 5a of the health care apparatus 5 of the health care center (step S29 in FIGS. 2A-2C). The administration records may be transmitted by the person 25 in charge via the Internet 21, or may be transmitted by the subscriber 1 via the cellular phone line 9 (step S52 in FIGS. 2A-2C). In either case, the transmitted administration records are recorded to the server 7a, and the record contents are transmitted to the cellular phone 10 of the subscriber 1 (steps S30, S53 in FIGS. 2A-2C).

In the case where all of the pharmaceuticals 24 that should be administered to the subscriber 1 have been administered thereto over the above operations, the operations of this health care system come to an end. Then, if distribution and administration of the pharmaceuticals 24 has been done, at least any one of the types, product names, quantities, drug prices, and selling prices of the pharmaceuticals 24 is added and recorded to an area within the server 7a where information related to the subscriber 1 has been stored and accumulated.

In addition, even if the subscriber 1 is a student who goes to school, it is needless to say that he or she can receive similar services at a health care department in the school such as school infirmary.

Further, in a case where the subscriber 1 does not attend the office 22 (in the cases of holidays, business trips, etc.), the subscriber 1 can receive similar services even at a town pharmacy 44 (steps S25-S30 in FIGS. 2A-2C). If the pharmacy has previously contracted with the health insurance society to which the subscriber 1 belongs, it is implementable to fulfill the viewing of diagnostic results of the subscriber 1 (step S27 in FIGS. 2A-2C), the distribution of the pharmaceuticals 24, the transmission and recording of distribution (administration) records to the transmitting/receiving section 5b of the health care apparatus 5 of the health care center, and the like by using the personal computer 26 connected to the Internet 21, or by using the cellular phone 10 of the subscriber 1, all as in the case of the services received by the health care room 23 (steps S29, S30 in FIGS. 2A-2C). Also, even if the pharmacy has not contracted with the health insurance society to which the subscriber 1 belongs, it becomes possible, given a permission by any one of the subscriber 1, the health care apparatus 5 of the health care center, and the health insurance society, to fulfill the viewing of diagnostic results of the subscriber 1, the selling of the pharmaceuticals 24, the transmission and recording of selling (administration) records to the transmitting/receiving section 5b of the health care apparatus 5 of the health care center, and the like in all. Further, it is much preferable that the place for reception of the pharmaceuticals 24, even if other than a pharmacy, is a highly convenient place for the subscriber 1, such as a convenience store or a station's kiosk. It is noted that the reckoning process for the charge of the pharmaceuticals 24 is, preferably, collectively implemented by the health care apparatus 5 of the health care center that performs centralized information control.

Furthermore, it is also possible that the subscriber 1 obtains and administers the pharmaceuticals 24 as the subscriber 1 stays at home 14. The subscriber 1 asks the pharmacy 44 to delivery the pharmaceuticals 24. The person 25 in charge of the pharmacy 44 prepares the pharmaceuticals 24, and a deliverer 45 delivers this to the subscriber 1 (steps S25, S40 in FIGS. 2A-2C). The delivered pharmaceuticals 24 may be based on information which has been acquired by the person 25 in charge accessing the home page 8 with a permission obtained from any one of the subscriber 1, the health care apparatus 5 of the health care center, and the health insurance society via the Internet 21, which is an example of the fourth transmission means, and the transmitting/receiving section 5b of the health care apparatus 5 of the health care center by using a personal computer 26 (steps S41, S42 in FIGS. 2A-2C), or may be notified by the subscriber 1 when the subscriber 1 requests the delivery (step S46 in FIGS. 2A-2C).

Upon completion of the delivery of the pharmaceuticals 24 to the subscriber 1, administration of the pharmaceuticals 24 to the subscriber 1 is performed automatically or manually (steps S43, S47 in FIGS. 2A-2C), and the administration records including the types, product names, quantities, drug prices, selling prices, and the like of the pharmaceuticals 24 are transmitted to the transmitting/receiving section 5a of the health care apparatus 5 of the health care center (step S44 in FIGS. 2A-2C). The administration records may be transmitted by the person 25 in charge via the Internet 21 or transmitted by the subscriber 1 via the cellular phone line 9 to the transmitting/receiving section 5a of the health care apparatus 5 of the health care center (step S48 in FIGS. 2A-2C). In either case, the transmitted administration records are recorded to the server 7a, and the record contents are transmitted to the cellular phone 10 of the subscriber 1 (steps S45, S49 in FIGS. 2A-2C).

In the case where all of the pharmaceuticals 24 that should be administered to the subscriber 1 have been administered to the subscriber 1 over the above operations, the operations of this health care system come to an end. Then, at least any one of the types, product names, quantities, drug prices, and selling prices of the pharmaceuticals 24 is added and recorded to an area within the server 7a where information related to the subscriber 1 has been stored and accumulated.

Next, advertisements of pharmaceuticals or health foods suited to diagnostic results of the subscriber 1 are explained. An advertising agency 31 permitted by the subscriber 1 and/or the health care apparatus 5 of the health care center and/or the health insurance society views the home page 8 via the Internet 35 and a transmitting/receiving section 5c of the health care apparatus 5 of the health care center. The advertising agency 31 has received requests for advertisements of commodity products from a plurality of clients 32a, 32b, . . .

, and from thereamong, selects pharmaceuticals suited to the health status of the subscriber 1. In this selection, for example, advertisements of commodities of pharmaceuticals or the like suited to the analytical data and/or diagnostic results are selected and disclosed to the test subject person. Here is explained a case where a commodity 'a' of a client 32a is suited. The advertising agency 31 instructs, via the Internet 36, a cable television station 33 to which the subscriber 1 has subscribed so as to put on-air a television commercial of the commodity 'a' during a program that the subscriber 1 is viewing. The cable television station 33 distributes the television commercial of the commodity 'a' via a cable television network 34, which is an example of the fifth transmission means, to a television (the advertisement disclosure means) 15 owned by the subscriber 1. For purchase of the commodity 'a', it is also possible that the subscriber 1 transmits his/her will of purchase to the cable television station 33 via the cable television network 34, and the client 32a makes delivery of the pharmaceutical.

As described hereinabove, by using this health care system, it becomes feasible for the subscriber 1 to enjoy proper medical services such as health advice or administration of pharmaceuticals at proper timing while keeping his/her own life pattern, and therefore to easily fulfill the daily health care or the onset control of various diseases.

It is noted that the present invention is not limited to the above embodiments, and may be embodying carried out in other various modes.

For example, the first embodiment has been described on cases where the first, second, third, and fourth transmission means are the Internet 4, the cellular phone line 9, the health-care-system exclusive line 11, and the Internet 21, as examples, respectively. However, each of those may be any one of a wire telephone line, a wireless telephone line, the Internet, a cable television network, and a health-care-system exclusive line without any problem. Besides, all or arbitrary two or arbitrary three means of the first, second, third, and fourth transmission means may preferably be implemented by any one of a wire telephone line, a wireless telephone line, the Internet, a cable television network, and a health-care-system exclusive line.

Also, although the first embodiment has been described on a case where the fifth transmission means is the cable television network 34, yet the fifth transmission means may be implemented by a wire telephone line, a wireless telephone line, the Internet, a cable television network, a health-care-system exclusive line, mail, a newspaper, or a home delivery service without any problem. Still, the communication medium for advertisements may be voice, e-mail, FAX, Internet advertisement, direct mail, newspaper advertisement, newspaper-inserted advertisement (an advertising leaflet), etc., in addition to television commercials, preferably in each case.

Further, although the first embodiment has been described on a case where the information terminal device owned by the subscriber 1 is the cellular phone 10, yet the information terminal device may be one that allows the subscriber 1 to perform the transmission and reception of information at his/her discretion, such as a fixed telephone, a personal computer, a PDA equipped with communication function, and a car navigation system equipped with communication function, without any problem.

Then, diagnostic results transmitted to the cellular phone 10 of the subscriber 1 may be via voice or e-mail, and are preferably fulfilled even by FAX or information input using the Internet or the like.

Also, the communication medium for the information related to administered pharmaceuticals, which is to be transmitted to the transmitting/receiving section 5a of the health care apparatus 5 of the health care center, may be voice, e-mail, FAX, information input using the Internet, or the like without any problem.

Further, the diagnostic results transmitted to the subscriber 1 may indeed be transferred to the subscriber 1 as mere voice information or text information, but it is much preferable that the subscriber 1 preparatorily sets the information terminal device such as a personal digital assistant (PDA) owned by the subscriber 1 (the cellular phone 10 in the first embodiment) so that an imaginary character at the subscriber 1's gusto notifies the subscriber 1 of the contents of diagnostic results or advice in a friendly manner (e.g., as voice information and/or image information). Whereas diagnostic results, health care advice, or nutritional advice, and the like often tend to be received as peremptory, coercive commands or instructions, such receptions can be relaxed more or less in the notification to the subscriber 1, so that the actual effect of this health care system is enhanced dramatically. As the imaginary character, preferably used are synthesized images or photographed images of existing entertainers, sport professionals, family, friends, and the like, dramatis personae's images of animations, personified animals, and the like.

According to the present invention, as described above, there are provided advantageous effects that a person receives proper medical services at proper timing, which makes it easily achievable for the person to maintain a good health status and prevent various diseases.

It is noted that properly combining any arbitrary embodiments among the foregoing various embodiments makes it possible to produce working effects of the individual embodiments.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

The invention claimed is:

1. A health care system comprising:
    a sampling device for sampling body fluid of the test subject;
    an analyzer processor configured to analyze the sampled body fluid;
    a diagnosis terminal configured to diagnose a health status of the test subject from analytical data obtained by said analyzer processor;
    a server computer configured to store and accumulate health care information, the health information including a diagnostic result of a diagnosis performed by said diagnosis terminal;
    a health-care-information display device in communication with the server computer, the health-care-information display device configured to receive the health care information and display the health care information; and
    a pharmaceutical administration device configured to prepare and administer a pharmaceutical to be administered to the test subject based on the diagnostic result; and
    a control processor for controlling an administration operation by said pharmaceutical administrative device,
    wherein said pharmaceutical administration device includes a pharmaceutical analyzer, said pharmaceutical administration device being configured to prepare a pharmaceutical described in a prescription contained in the diagnostic result, said pharmaceutical analyzer being configured to use a micro total analysis system (TAS) to analyze the prepared pharmaceutical and compare a result of the analysis with the pharmaceutical described in the prescription contained in the diagnostic result, and said pharmaceutical administration device configured to administer said pharmaceutical prepared by said pharmaceutical administration device to the test subject when said pharmaceutical prepared by said pharmaceutical administration device matches the pharmaceutical described in the prescription contained in the diagnostic result.

2. The health care system as claimed in claim 1, wherein: said display device receives the diagnostic result and displays the diagnostic result.

3. The health care system as claimed in claim 1, wherein: said diagnosis terminal comprises a first diagnosis terminal and a second diagnosis terminal ; and said server computer comprises a first server computer and a second server computer, such that when the analytical data have departed from a permissible range indicating a state of healthiness, said first diagnosis terminal transmits the analytical data to said second diagnosis terminal and said second server computer, and the health status of the test subject is diagnosed from the transmitted analytical data with said second diagnosis terminal, and said display device displays a diagnostic result generated by said second diagnosis terminal after the diagnostic result is transmitted to said display device.

4. The health care system as claimed in claim 1, wherein: said server computer stores and accumulates personal data of the test subject including historical personal data, allergy data and genetic information data, wherein the historical personal data includes:
historical data of analytical data;
historical data of diagnostic results;
historical data of pharmaceutical administration; and
historical data of effects of pharmaceutical administration given to the test subject; and
said diagnosis terminal performs a diagnosis based on the personal data of the test subject.

5. The health care system as claimed in claim 1, wherein: said server computer stores and accumulates personal data of test subjects including historical personal data, allergy data and genetic information data, wherein the historical personal data includes:
historical data of analytical data;
historical data of diagnostic results;
historical data of pharmaceutical administration; and
historical data of effects of pharmaceutical administration given to the test subject, for making the personal data of the test subjects available as an integrated database that has been analyzed and statistically processed on a subscriber basis; and
said diagnosis terminal performs a diagnosis based on the integrated database and the personal data stored and accumulated in said server computer.

6. The health care system as claimed in claim 1, further comprising a disclosure device configured to disclose at least one of the analytical data and the diagnostic result to at least any one of the test subject, a person permitted by the test subject, and a person permitted by a health care organization to which the test subject belongs.

7. The health care system as claimed in claim 1, wherein at least one of the analytical data and the diagnostic result stored and accumulated in said server computer are stored and accumulated in said server computer as at least one of the analytical data and the diagnostic result, and a pharmaceutical administered to the test subject is associated with the at least one of the analytical data and the diagnostic result.

8. The health care system as claimed in claim 1, wherein:
said server computer stores and accumulates constitutional data related to the constitution of an allergy of the test subject and the genetic information data of the test subject; and
said diagnosis terminal queries one of the constitutional data related to the constitution of an allergy of the test subject and the genetic information data of the test subject stored and accumulated in said server computer to implement disclosure of advice effective for the test subject or administration and preparation of a pharmaceutical effective for the test subject as the diagnostic result.

9. The health care system as claimed in claim 1, wherein the control processor controls one of a dosing time, a quantity of the pharmaceutical, and a type of the pharmaceutical, by considering at least a physical condition of the test subject, pharmaceuticals that have already been administered to the test subject, and pharmaceuticals that are scheduled to be administered to the test subject.

10. The health care system as claimed in claim 1, further comprising a sleep-state detection device configured to detect a sleep state of the test subject, wherein upon confirming that the test subject is in a sleep-state with said sleep-state detection device, said control processor administers the pharmaceutical to the test subject.

11. The health care system as claimed in claim 1, wherein at least one of a type, a product name, a quantity, a drug price, and a selling price of a pharmaceutical that has been administered to the test subject by said pharmaceutical administration device is recorded to an area within said server computer where information related to the test subject is stored and accumulated.

12. The health care system as claimed in claim 1, further comprising an advertisement disclosure device configured to disclose to the test subject an advertisement of a commodity of a pharmaceutical adapted to at least one of the displayed analytical data and the diagnostic result.

13. The health care system as claimed in claim 1, wherein a diagnostic result transmitted to the test subject is transferred to the test subject by at least one of voice information and image information by a character previously set based on the vitality of the test subject.

14. The health care system as claimed in claim 1, wherein the pharmaceutical analyzer is configured to stop administration of said pharmaceutical prepared by said pharmaceutical administration device to the test subject when said pharmaceutical prepared by said pharmaceutical administration device does not match the pharmaceutical described in the prescription contained in the diagnostic result.

* * * * *